United States Patent
Li et al.

(10) Patent No.: US 11,261,196 B2
(45) Date of Patent: Mar. 1, 2022

(54) SALT SERVING AS AKT INHIBITOR AND CRYSTAL THEREOF

(71) Applicant: HARBIN ZHENBAO PHARMACEUTICAL CO., LTD., Heilongjiang (CN)

(72) Inventors: Gang Li, Shanghai (CN); Lun Lu, Shanghai (CN); Qingqing Lu, Shanghai (CN); Lihong Hu, Shanghai (CN); Charles Z. Ding, Shanghai (CN)

(73) Assignee: HARBIN ZHENBAO PHARMACEUTICAL CO., LTD., Heilongjiang (CN)

( * ) Notice: Subject to any disclaimer, the term of this patent is extended or adjusted under 35 U.S.C. 154(b) by 0 days.

(21) Appl. No.: 16/772,322

(22) PCT Filed: Dec. 12, 2018

(86) PCT No.: PCT/CN2018/120531
§ 371 (c)(1),
(2) Date: Jun. 12, 2020

(87) PCT Pub. No.: WO2019/114741
PCT Pub. Date: Jun. 20, 2019

(65) Prior Publication Data
US 2021/0087205 A1    Mar. 25, 2021

(30) Foreign Application Priority Data

Dec. 13, 2017 (CN) .......................... 201711331448.1

(51) Int. Cl.
*A61K 31/55* (2006.01)
*C07D 495/14* (2006.01)

(52) U.S. Cl.
CPC ............ *C07D 495/14* (2013.01); *A61K 31/55* (2013.01); *C07B 2200/13* (2013.01)

(58) Field of Classification Search
CPC .... A61K 31/519; A61K 9/0014; A61K 45/06; A61K 31/55; A61P 17/06; A61P 17/16;
(Continued)

(56) References Cited

U.S. PATENT DOCUMENTS 8,273,782 B2    9/2012  Seefeld et al.
10,654,868 B2   5/2020  Lu et al.
(Continued)

FOREIGN PATENT DOCUMENTS

CN    1639151 A     7/2005
CN    101646427 A   2/2010
(Continued)

OTHER PUBLICATIONS

Extended European search report issued in European patent application No. EP18887717, dated Oct. 15, 2020.
(Continued)

*Primary Examiner* — Taylor V Oh
(74) *Attorney, Agent, or Firm* — Harness, Dickey & Pierce, P.L.C.

(57) ABSTRACT

A salt serving as an Akt inhibitor and a crystal thereof, specifically related to a salt of the compound of formula (I) and a crystal thereof.

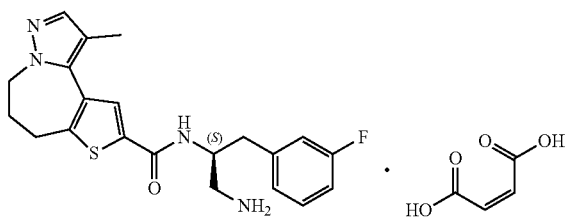

20 Claims, 3 Drawing Sheets

(58) Field of Classification Search
CPC .. A61P 35/00; A61P 29/00; A61P 3/10; A61P 19/02; C07D 495/14; C07B 2200/13
USPC .......................................... 514/214, 214.02
See application file for complete search history.

(56) References Cited

U.S. PATENT DOCUMENTS

| | | |
|---|---|---|
| 2003/0181716 A1 | 9/2003 | Friebe et al. |
| 2010/0041726 A1 | 2/2010 | Seefeld et al. |

FOREIGN PATENT DOCUMENTS

| | | |
|---|---|---|
| CN | 201711331448.1 | 12/2017 |
| EP | 2002836 A1 | 12/2008 |
| JP | 2010518110 A | 5/2010 |
| JP | 6900406 B2 | 7/2021 |
| KR | 10-2019-0017996 A | 2/2019 |
| WO | WO-2007076423 A2 | 7/2007 |
| WO | WO-2008065054 A1 | 6/2008 |
| WO | WO-2008098104 A1 | 8/2008 |
| WO | WO-2009158371 A1 | 12/2009 |
| WO | WO-2017215588 A1 | 12/2017 |

OTHER PUBLICATIONS

Florence et al.: "Polymorph screening in pharmaceutical development" European Pharmaceutical Review, Kent: Russell Publ, US, No. 4, Aug. 19, 2010, pp. 28-33, XP009151199, ISSN: 1351-1599.
Written Opinion of the International Searching Authority issued in International Patent Application No. PCT/CN2018/120531 dated Dec. 3, 2019.
International Search Report issued in International Patent Application No. PCT/CN2018/120531 dated Dec. 3, 2019.
Aug. 31, 2021, First Office Action issued in Japanese application No. 2020-532703.
Nov. 19, 2021 the First Office Action issued in Korean application No. 2020-7020007.

SALT SERVING AS AKT INHIBITOR AND CRYSTAL THEREOF

CROSS-REFERENCE TO RELATED APPLICATIONS

This application is a 371 National Phase of International Application No. PCT/CN2018/120531, filed Dec. 12, 2018, which claims the benefit of Chinese Patent Application No. CN 201711331448.1, filed Dec. 13, 2017. The entire disclosures of the above applications are incorporated herein by reference.

FIELD OF INVENTION

The present invention relates to a salt form serving as an Akt inhibitor and a crystal form thereof, specifically related to a salt form of the compound of formula (I) and a crystal form thereof, and also relates to a use of the salt form and crystal form in manufacturing a medicament for treating tumors, diabetes and rheumatoid arthritis.

PRIOR ARTS

Akt, also known as protein kinase B (PKB), is a serine/threonine protein kinase with a molecular weight of approximately 60 kDa, it is located at an important intersection of multiple signaling pathways and can regulate cytokines, growth factors and cell survival signals activated by oncogene Ras, and it is ubiquitous in eukaryotic regulatory networks. The Akt signaling pathway is closely related to the occurrence and development of various diseases such as malignant tumors, diabetes, rheumatoid arthritis, etc., and it is therefore getting more and more attention. In recent years, the continuous in-depth researches not only enable people have a deeper understanding of the biological role of Akt, but also have made many major breakthroughs in the study of the regulatory mechanism of the Akt signaling pathway, its specific role in some human diseases and its molecular regulation mechanism are gradually being elucidated.

Akt consists of four parts: a N-terminal regulatory region, a intermediate enzyme active region, a C-terminal regulatory region, and a hinge region connecting the PH region and the kinase active region. The N-terminal regulatory region has a platelet-leukocyte c-kinase homologous region (i.e. PH region), its exact mechanism during signal transduction is unclear; the intermediate enzyme active region has catalytic activity for the phosphorylation of serine/threonine residues, wherein the phosphorylation at the Thr308 site in the variable peptide loop (T-loop) is required for the activation of Akt; the C-terminal has a proline-rich hydrophobic domain (HM), which contains a second phosphorylation site Ser473 essential for the complete activation of Akt. In recent years, the corresponding crystal structures of each structural regions have been successively analyzed, and the key phosphorylation sites, ATP binding sites and protein substrate binding sites have also been more deeply understood, which has laid the foundation for the development of the small molecules specific inhibitor of Akt/PKB.

At least three subtypes of Akt have currently been found in mammals: Akt1 (PKBα), Akt2 (PKBβ) and Akt3 (PKBγ), which are encoded by three different genes located on chromosomes 14q32, 19q13 and 1q43 respectively, with 85% of the sequence homology belongs to the AGC protein kinase family. Studies on mouse embryonic fibroblasts have found that different Akt subtype-deficient strains eventually lead to different phenotypes: Akt1 deficiency manifests as placental dystrophy, growth delay and weight loss, Akt2 deficiency is characterized by abnormal insulin and blood glucose, and Akt3 deficiency shows a reduction in brain volume. In human diseases, the expression and effects of the three Akt subtypes are also significantly different.

Akt can be activated by various intracellular substances such as hormones, growth factors, cytokines, and intercellular matrix, etc. Akt locates at the center of the PI3K/Akt pathway and is a direct target gene of PI3K. Many cytokines, growth factors, and physical stimuli can phosphorylate Akt by activating PI3K. In general situation, the phosphorylation of Akt can be used as an indicator to measure the activity of PI3K.

The study of the physiological function of Akt is inseparable from the discovery of its substrate. So far, more than 100 types of Akt substrates have been discovered. The three subtypes of Akt and its diverse substrates are the structural basis for its multiple functions. Activated Akt affects the activation state of a series of downstream effector molecules through various signaling pathways, and exerts the biological effects of inhibiting apoptosis and promoting proliferation in cells.

The Akt pathway intersects with many signaling pathways to form a complex signaling network. Under certain circumstances, the Akt pathway can activate the NF-κB pro-survival signal or inhibit the JNK/p38 apoptotic signal, but the mode of action between p38 and Akt is still inconclusive. The interaction between the PI3K/Akt pathway and the Ras/MAPK pathway significantly manifests in different stages of these two pathways, regardless of different cell types, different cell differentiation stages, and different experimental conditions, but whether Akt pathway positively or negatively regulates the Ras/MAPK pathway and what kind of regulation is dominant in a certain cell have not yet been fully revealed. The Akt signaling pathway is closely related to the occurrence and development of diseases such as tumors and rheumatoid arthritis, the interconnection and influence of the various pathways may jointly play an important role in the occurrence of the diseases.

References: WO/2008/098104, WO2009/158371A1.

Different solid forms of active pharmaceutical ingredients may have different properties. Changes in the properties of different solid forms can provide improved formulations, for example, easy synthesis or treatment, improved stability and expiration date. Changes in properties caused by different solid forms can also improve the final dosage form. Different solid state forms of active pharmaceutical ingredients can also provide polycrystals or other crystal forms, thereby providing more opportunities to evaluate the changes in properties of the active pharmaceutical ingredient of a solid.

Technical Effect

The preparation method of the salt form and crystal form of the compound of formula (I) of the present disclosure is simple, and the crystal form is relatively stable, and less affected by heat and humidity, and can be easily made into preparations.

CONTENT OF THE PRESENT DISCLOSURE

In one aspect, the present disclosure provides a compound of formula (I),

In another aspect, the present disclosure provides a crystal form of the compound of formula (I), wherein the X-ray powder diffraction pattern thereof comprises characteristic diffraction peaks at the following angle 2θ: 12.25°±0.2°, 14.46°±0.2° and 21.83°±0.2°.

In some embodiments of the present disclosure, the X-ray powder diffraction pattern of the crystal form of the compound of formula (I) comprises characteristic diffraction peaks at the following angle 2θ: 8.50°±0.2°, 10.20°±0.2°, 12.25°±0.2°, 14.46°±0.2°, 15.30°±0.2°, 21.83°±0.2°, 27.31°±0.2° and 31.41°±0.2°.

Figure 1:
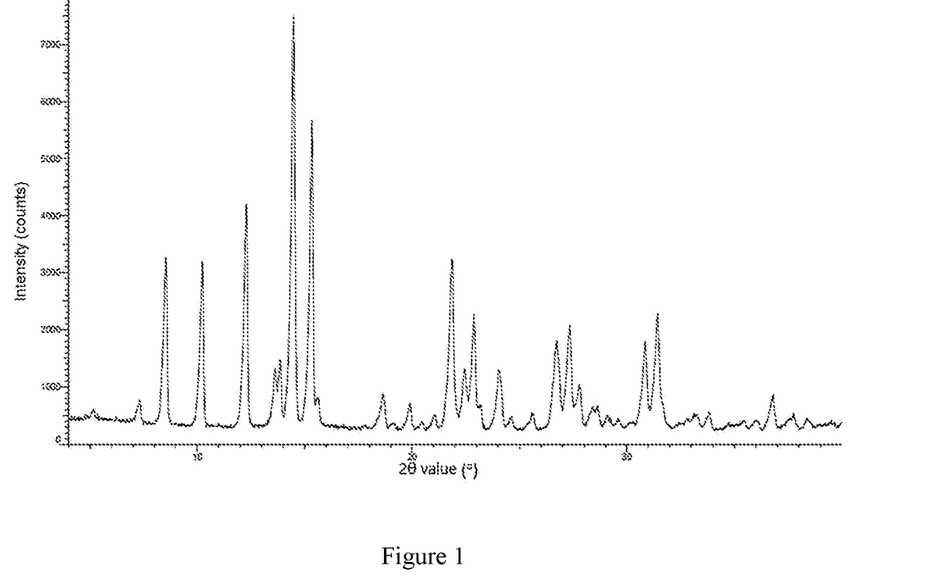
FIG. 1 is the XRPD pattern of the crystal form of the compound of formula (I).

In some embodiments of the present disclosure, the X-ray powder diffraction pattern of the crystal form of the compound of formula (I) is as shown in FIG. 1.

In some embodiments of the present disclosure, the analytical data of the X-ray powder diffraction pattern of the crystal form of the compound of formula (I) is as shown in Table 1.

TABLE 1

Analytical data of the XRPD pattern of the crystal form of the compound of formula (I)

| No. | 2θ Angle (°) | d-spacing (Å) | Relative intensity (%) |
|---|---|---|---|
| 1 | 4.860 | 18.169 | 1.0 |
| 2 | 5.139 | 17.181 | 2.0 |
| 3 | 5.373 | 16.434 | 0.8 |
| 4 | 7.273 | 12.145 | 4.9 |
| 5 | 8.503 | 10.390 | 39.7 |
| 6 | 10.202 | 8.663 | 37.7 |
| 7 | 12.254 | 7.217 | 53.0 |
| 8 | 13.668 | 6.474 | 12.1 |
| 9 | 13.815 | 6.405 | 14.1 |
| 10 | 14.460 | 6.121 | 100.0 |
| 11 | 15.303 | 5.785 | 69.3 |
| 12 | 15.578 | 5.684 | 6.7 |
| 13 | 17.797 | 4.980 | 0.7 |
| 14 | 18.632 | 4.759 | 7.7 |
| 15 | 19.091 | 4.645 | 1.4 |
| 16 | 19.876 | 4.463 | 6.1 |
| 17 | 20.449 | 4.440 | 2.0 |
| 18 | 21.031 | 4.221 | 3.2 |
| 19 | 21.834 | 4.067 | 42.5 |
| 20 | 22.448 | 3.957 | 14.5 |
| 21 | 22.859 | 3.887 | 28.4 |
| 22 | 23.106 | 3.846 | 5.5 |
| 23 | 24.060 | 3.696 | 14.6 |
| 24 | 24.591 | 3.617 | 2.6 |
| 25 | 25.574 | 3.480 | 3.9 |
| 26 | 25.593 | 3.478 | 3.6 |
| 27 | 26.733 | 3.332 | 22.0 |
| 28 | 27.310 | 3.263 | 24.4 |
| 29 | 27.771 | 3.210 | 10.1 |
| 30 | 28.441 | 3.136 | 4.1 |
| 31 | 28.571 | 3.122 | 4.3 |
| 27 | 29.106 | 3.066 | 2.7 |
| 28 | 29.594 | 3.016 | 2.0 |
| 29 | 30.229 | 2.954 | 1.2 |
| 30 | 30.837 | 2.897 | 21.5 |
| 31 | 31.409 | 2.846 | 27.6 |
| 32 | 32.829 | 2.726 | 2.0 |
| 33 | 32.513 | 2.752 | 1.1 |
| 34 | 32.832 | 2.726 | 1.8 |
| 35 | 33.201 | 2.696 | 3.1 |
| 36 | 33.800 | 2.650 | 4.2 |
| 37 | 34.771 | 2.578 | 0.7 |
| 38 | 35.149 | 2.551 | 0.9 |
| 39 | 35.402 | 2.533 | 1.6 |
| 40 | 36.021 | 2.491 | 2.0 |
| 41 | 36.764 | 2.443 | 7.0 |
| 42 | 37.624 | 2.389 | 2.4 |
| 43 | 37.724 | 2.383 | 3.0 |
| 44 | 38.410 | 2.342 | 2.5 |
| 45 | 39.218 | 2.295 | 1.0 |
| 46 | 39.516 | 2.279 | 1.2 |

In some embodiments of the present disclosure, the DSC pattern of the crystal form of the compound of formula (I) has an endothermic peak with an onset of 195.10° C.±3° C., and has an exothermic peak with an onset of 209.23° C.±3° C.

Figure 2:
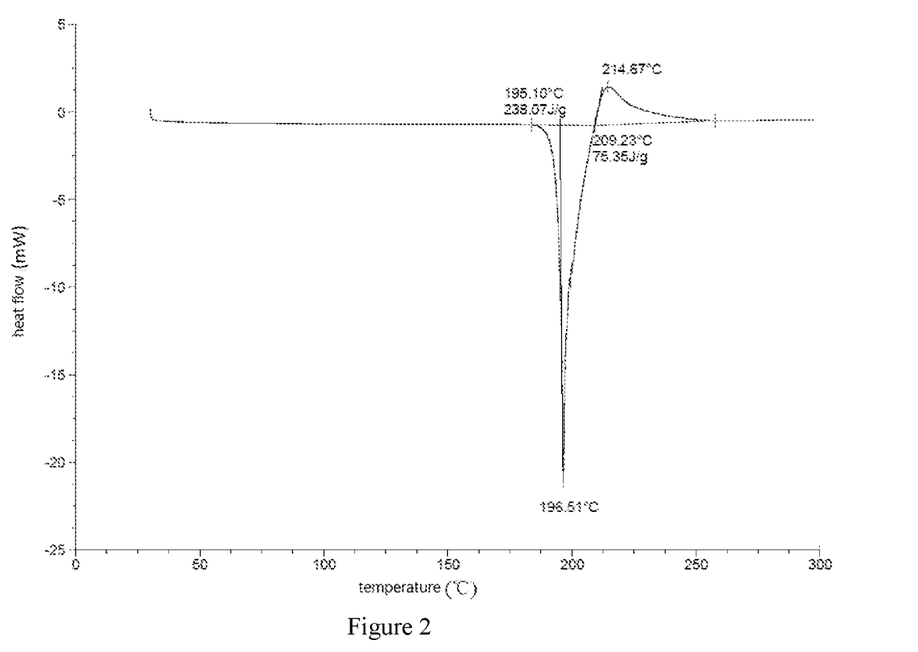
FIG. 2 is the DSC pattern of the crystal form of the compound of formula (I).

In some embodiments of the present disclosure, the DSC pattern of the crystal form of the compound of formula (I) is as shown in FIG. 2.

In some embodiments of the present disclosure, the TGA pattern of the crystal form of the compound of formula (I) has a weight loss of 0.295% occurred at 100.00° C.±3° C.

Figure 3:
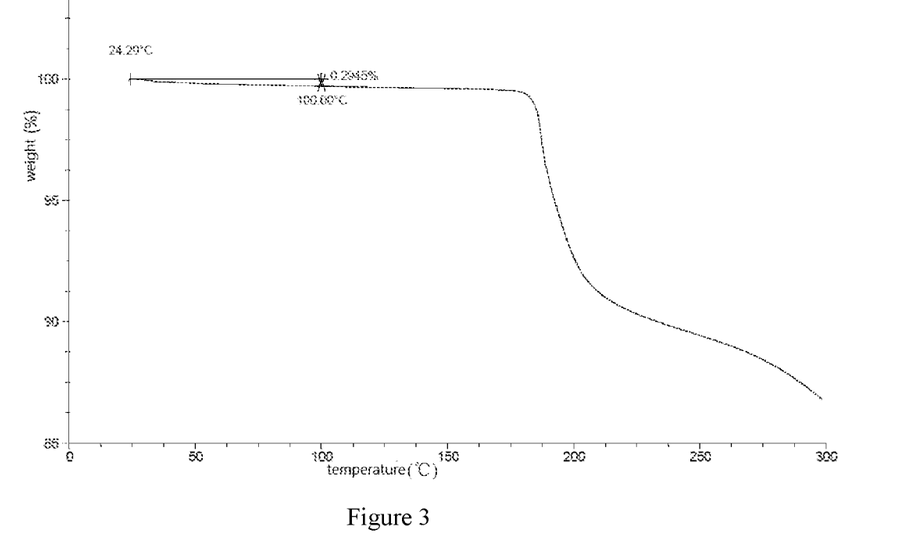
FIG. 3 is the TGA pattern of the crystal form of the compound of formula (I).

In some embodiments of the present disclosure, the TGA pattern of the crystal form of the compound of formula (I) is as shown in FIG. 3.

In some embodiments of the present disclosure, the infrared spectrum of the crystal form of the compound of formula (I) comprises characteristic absorption peaks at 3316 $cm^{-1}$±5 $cm^{-1}$, 3079 $cm^{-1}$±5 $cm^{-1}$, 3058 $cm^{-1}$±5 $cm^{-1}$, 3016 $cm^{-1}$±5 $cm^{-1}$, 2954 $cm^{-1}$±5 $cm^{-1}$, 2935 $cm^{-1}$±5 $cm^{-1}$, 2915 $cm^{-1}$±5 $cm^{-1}$, 2902 $cm^{-1}$±5 $cm^{-1}$, 2864 $cm^{-1}$±5 $cm^{-1}$, 1704 $cm^{-1}$±2 $cm^{-1}$, 1633 $cm^{-1}$±2 $cm^{-1}$, 1623 $cm^{-1}$±2 $cm^{-1}$, 1589 $cm^{-1}$±2 $cm^{-1}$, 1530 $cm^{-1}$±2 $cm^{-1}$, 1514 $cm^{-1}$±2 $cm^{-1}$, 1486 $cm^{-1}$±2 $cm^{-1}$, 1445 $cm^{-1}$±2 $cm^{-1}$, 1429 $cm^{-1}$±2 $cm^{-1}$, 1408 $cm^{-1}$±2 $cm^{-1}$, 1395 $cm^{-1}$±2 $cm^{-1}$, 1373 $cm^{-1}$±2 $cm^{-1}$, 1359 $cm^{-1}$±2 $cm^{-1}$, 1345 $cm^{-1}$±2 $cm^{-1}$, 1332 $cm^{-1}$±2 $cm^{-1}$, 1282 $cm^{-1}$±2 $cm^{-1}$, 1247 $cm^{-1}$±2 $cm^{-1}$, 1214 $cm^{-1}$±2 $cm^{-1}$, 1173 $cm^{-1}$±2 $cm^{-1}$, 1135 $cm^{-1}$±2 $cm^{-1}$, 1114 $cm^{-1}$±2 $cm^{-1}$, 1054 $cm^{-1}$±2 $cm^{-1}$, 1030 $cm^{-1}$±2 $cm^{-1}$, 1000 $cm^{-1}$±2 $cm^{-1}$, 952 $cm^{-1}$±2 $cm^{-1}$, 914 $cm^{-1}$±2 $cm^{-1}$, 902 $cm^{-1}$±2 $cm^{-1}$, 883 $cm^{-1}$±2 $cm^{-1}$, 861 $cm^{-1}$±2 $cm^{-1}$, 839 $cm^{-1}$±2 $cm^{-1}$, 825 $cm^{-1}$±2 $cm^{-1}$, 789 $cm^{-1}$±2 $cm^{-1}$, 763 $cm^{-1}$±2 $cm^{-1}$, 736 $cm^{-1}$±2 $cm^{-1}$, 720 $cm^{-1}$±2 $cm^{-1}$ and 704 $cm^{-1}$±2 $cm^{-1}$.

Figure 4:
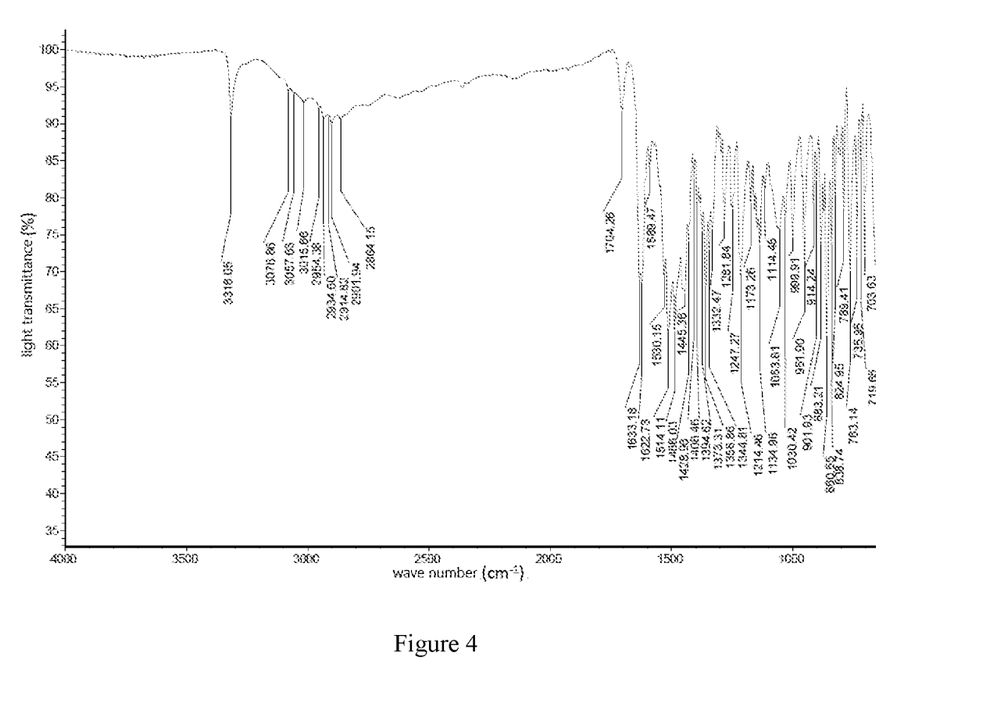
FIG. 4 is the infrared absorption spectrogram of the crystal form of the compound of formula (I).

In some embodiments of the present disclosure, the infrared spectrum of the crystal form of the compound of formula (I) is as shown in FIG. 4.

Definitions and Explanations

Unless otherwise indicated, the following terms and phrases used herein are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The intermediate compounds of the present disclosure can be prepared by various synthetic methods known to those skilled in the art, including the embodiments described below, the embodiments formed by combining the embodiments described below with other chemical synthesis methods, and equivalent alternatives well-known for those skilled in the art. Preferred embodiments include, but are not limited to, the embodiments of the present disclosure.

The chemical reactions of the embodiments of the present disclosure are carried out in a suitable solvent, and the solvent should be suitable for the chemical change, and the reagents and materials required therefor of the present disclosure. In order to obtain the compounds of the present disclosure, it is sometimes necessary for those skilled in the art to modify or select the synthetic steps or reaction schemes based on the existing embodiments.

The present invention will be specifically described below by way of embodiments, but the scope of the present invention is not limited thereto.

All solvents used in the present disclosure are commercially available and can be directly used without further purification.

The solvents used in the present disclosure are commercially available.

The present disclosure employs the following abbreviations:

TBTU: O-benzotriazole-N, N, N', N'-tetramethyluronium tetrafluoroborate; DIEA: N, N-diisopropylethylamine; DMF: N, N-dimethylformamide; MeOH: methanol; THF: tetrahydrofuran; Pd(dppf)Cl$_2$: [1,1'-bis (diphenylphosphino) ferrocene] palladium dichloride; Pd$_2$(dba)$_3$: tris (dibenzylideneacetone) dipalladium; x-PHOS: 2-dicyclohexylphosphino-2,4,6-triisopropylbiphenyl The Instrument and Analysis Method of the Present Disclosure:

1.1 X-Ray Powder Diffractometer (XRPD)

Instrument model: Bruker D8 advance X-ray diffractometer

Detection method: about 10-20 mg of the sample was used for XRPD detection.

The detailed XRPD parameters were as follows:

X-ray tube: Cu, kα, (λ=1.54056 Å).

X-ray tube voltage: 40 kV, X-ray tube current: 40 mA

Divergence slit: 0.60 mm

Detector slit: 10.50 mm

Anti-scattering slit: 7.10 mm

Scanning range: 3 or 4-40 deg

Step size: 0.02 deg

Step time: 0.12 seconds

Rotation speed of sample tray: 15 rpm 1.2 Differential Scanning Calorimeter (DSC)

Instrument Model: TA DSC Q2000 differential scanning calorimeter

Detection method: samples (0.5-1 mg) were placed in a DSC aluminum crucible for detection, and heated from room temperature (25° C.) to 300° C. or 350° C. with a heating rate of 10° C./min under the condition of 50 mL/min N$_2$.

1.3 Thermal Gravimetric Analyzer (TGA)

Instrument Model: TA Q5000 thermal gravimetric analyzer

Detection method: samples (2 mg to 5 mg) were placed in a TGA platinum crucible for detection, and heated from room temperature (25° C.) to 300° C., 350° C. or a weight loss of 20% occurred with a heating rate of 10° C./min under the condition of 25 mL/min N$_2$.

1.4 Dynamic Vapor Sorption (DVS)

Instrument model: DVS Advantage-1 (SMS)

Detection conditions: samples (10 mg to 15 mg) were used for DVS detection.

Equilibrium: dm/dt=0.01%/min (time: 10 min to maximum 180 min)

Drying: 120 minutes at 0% RH

RH (%) gradient for testing: 10%

RH (%) gradient range for testing: 0%-90%-0%

The hygroscopicity was evaluated using the following scales in Table 2:

TABLE 2

| Scales used for hygroscopicity evaluation | |
|---|---|
| Scales for hygroscopicity | Hygroscopic weight gain* |
| Deliquescence | Absorbing sufficient water to form liquid |
| High hygroscopicity | Hygroscopic weight gain ≥15% |
| Medium hygroscopicity | 15% > Hygroscopic weight gain ≥2% |
| Low hygroscopicity | 2% > Hygroscopic weight gain ≥0.2% |
| No or almost no hygroscopicity | Hygroscopic weight gain <0.2% |

*Hygroscopic weight gain at 25° C./80% RH 1.5 High Performance Liquid Chromatograph (HPLC)

Instrument model: Agilent 1200 high performance liquid chromatograph

The analysis method is as follows:

TABLE 3

| HPLC analysis method for content test of related substance | | | |
|---|---|---|---|
| Instrument | Agilent 1200 high performance liquid chromatograph | | |
| Chromatographic | Ascentis Express C18, 4.6 × 150 mm, 2.7 μm (94#) | | |
| Mobile phase A | 0.1% Phosphoric acid aqueous solution | | |
| Mobile phase B | Acetonitrile solution | | |
| Flow rate | 1.0 mL/min | | |
| Injection volume | 10.0 μL | | |
| Detection wavelength | 210 nm | | |
| Column temperature | 40° C. | | |
| Diluent | Acetonitrile/pure water = 1/1 (v/v) | | |
| Gradient elution procedure | Time (min) | Mobile phase A | Mobile phase B (%) |
| | 0.00 | 95 | 5 |
| | 5.00 | 95 | 5 |
| | 25.00 | 5 | 95 |
| | 27.00 | 5 | 95 |
| | 27.01 | 95 | 5 |
| | 30.00 | 95 | 5 |

DETAILED DESCRIPTION OF THE EMBODIMENTS

The present disclosure is described in detail through the embodiments, which does not mean any adverse limitation of the present disclosure. The present disclosure has been described in detail herein, wherein the specific embodiments thereof are also disclosed, for those skilled in the art, it's obvious that various changes and improvements can be made to the specific embodiments of the present disclosure without departing from the spirit and scope of the present disclosure.

Preparation Embodiment

1-A

1-B

1-C          1-D

1-E

1-L

1-M

Crystal form of the compound of formula (I)

Step 1: Synthesis of Intermediate 1-B

Compound 1-A (5.0 Kg, 60.9 mol) was dissolved in anhydrous toluene (7 L), the obtained solution was added into a 50 L reaction kettle, and then dihydropyran (5.6 Kg, 60.9 mol) and trifluoroacetic acid (50 mL) were sequentially added thereto. The external temperature of the reaction kettle was set to 80° C., the solution was allowed to react while stirring overnight, and the completion of the reaction was monitored by HPLC. Ethyl acetate (10 L) and water (2 L) were added to the solution, and the obtained mixture was stirred, let stand, and subjected to liquid separation. The organic phase was washed with water (1 L×2) and concentrated to dryness by rotary evaporation to obtain intermediate 1-B, which is light yellow oily liquid. LCMS (ESI) m/z: 167 (M+1); $^1$H NMR (400 MHz, CDCl$_3$): δ ppm 1.66-1.67 (m, 3H), 2.02-2.08 (m, 6H), 3.66-3.72 (m, 1H), 4.03-4.07 (m, 1H), 5.30-5.33 (dd, J=10.0, 2.8 Hz, 1H), 7.37-7.38 (d, J=6.0 Hz, 1H).

Step 2: Synthesis of Intermediate 1-C

Under the protection of nitrogen, compound 1-B (2.0 Kg, 12.03 mol) was dissolved in anhydrous tetrahydrofuran (12 L), the obtained solution was added to a 50 L spherical kettle, cooled to −40° C. to −20° C., n-butyl lithium (5.3 L, 13.24 mol) was added dropwise into the solution, after the completion of the addition, the solution was allowed to react at this temperature while stirring for 1 hour, then isopropyl pinacolyl borate (2.351 Kg, 12.63 mol) was added dropwise thereto, after the completion of the addition, the cooling bath was removed, the reaction was continued while stirring for 40 minutes, and the completion of the reaction was monitored by HPLC. A saturated aqueous solution of ammonium chloride (2 L) were added dropwise to terminate the reaction, then 6N HCl was added to adjust pH value to 5-6, 20 L of water was added, and the solution was extracted once with 5 L of ethyl acetate, followed by extracting again with ethyl acetate (3 L). The organic phases were combined and concentrated to dryness by rotary evaporation to obtain intermediate 1-C, which is yellow solid. LCMS (ESI) m/z: 293 (M+1); $^1$H NMR (400 MHz, CDCl$_3$): δ ppm 1.356 (s, 12H), 1.54-1.57 (m, 1H), 1.70-1.72 (m, 2H), 1.99-2.00 (m, 1H), 2.08-2.09 (m, 1H), 2.23 (s, 3H), 2.45-2.51 (m, 1H), 3.63-3.70 (m, 1H), 4.02-4.06 (m, 1H), 5.81-5.84 (dd, J=10.0, 2.4 Hz, 1H), 7.40 (s, 1H).

Step 3: Synthesis of Intermediate 1-D

Under 0 to 20° C., 1-C (3.75 Kg, 10.64 mol) was added to a solution of hydrogen chloride in methanol (4 N, 16 L, 64 mol) while stirring, and the solution was allowed to react at about 20° C. while stirring overnight, and the completion of the reaction was monitored by HPLC. The reaction solution was concentrated until no solvent was evaporated, 4 L petroleum ether was added into the residue, the obtained mixture was stirred and let stand, the supernatant was poured out, the lower residue was slightly concentrated to dryness by rotary evaporation, then solid was precipitated and filtered, the filter cake was slurried with 1.5 L ethyl acetate and filtered, the filter cake was slurried again with 1.5 L ethyl acetate, the filter cake was collected, the filtrate was combined and the above operations was repeated, the filter cake was collected for another time, the filter cake was combined and dried under reduced pressure to obtain intermediate 1-D, which is white solid. LCMS (ESI) m/z: 209 (M+1); $^1$H NMR (CD$_3$OD): δ ppm 1.22-1.42 (d, 12H), 2.27-2.34 (d, 3H), 8.03-7.14 (d, 1H).

Step 4: Synthesis of Intermediate 1-F

Under 20 to 25° C., 1-E (2502.05 g, 10.64 mol), DMF (12.5 L), triethylamine (2.24 L, 16.09 mol) and Pd (dppf)Cl$_2$ (84.00 g, 0.115 mol) were added sequentially into a 50 L reaction kettle, then nitrogen gas was bubbled into the reaction solution for 10 minutes, and propynol (943 mL, 15.95 mol) was added dropwise into the reaction kettle. Under the protection of nitrogen, the temperature was raised to 60° C., the reaction was carried out at this temperature for 1 hour, then the temperature was raised to 80° C., and the reaction was carried out at this temperature for about 6.5 hours, and the completion of the reaction was monitored by HPLC. The obtained mixture was cooled to room temperature, ethyl acetate (20 L) and hydrochloric acid (2N, 1 L) were added into the mixture, then the mixture was stirred and subjected to liquid separation, the aqueous phase was extracted with ethyl acetate (5 L) once, the combined organic phases were washed with water (5 L×2) and concentrated to dryness by rotary evaporation, the residue was eluted by silica gel column (petroleum ether to petroleum ether/ethyl acetate=3/1), the eluent was concentrated to dryness by rotary evaporation to obtain intermediate 1-F, which is yellow solid. LCMS (ESI) m/z: 211 (M+1); $^1$H NMR (400 MHz, CDCl$_3$): δ ppm 1.39 (t, J=7.15 Hz, 3H), 1.78-1.88 (m, 1H), 4.30-4.42 (m, 2H), 4.50-4.59 (m, 2H), 7.13-7.20 (m, 1H), 7.61-7.70 (m, 1H).

Step 5: Synthesis of Intermediate 1-G

1-F (4039.55 g, 19.1 mol) was dissolved in 24 L of ethanol (mass fraction 95%), then triethylamine (20 mL, 0.144 mol) was added, the mixture was mixed well, and then evenly placed into twenty 2 L hydrogenation bottles. Under the protection of nitrogen, wet palladium on carbon (419.89 g, 10%) was evenly placed into the above hydrogenation bottles, hydrogen replacement was performed for 2 times, the hydrogen pressure was set to 345 kPa (50 PSI), and the temperature was set to 25° C., the reaction was carried out for about 3 hours, and the completion of the reaction was monitored by HPLC. The mixture was filtered, and the filtrate was combined and concentrated to dryness by rotary evaporation, 0.1N hydrochloric acid (3 L) and ethyl acetate (6 L) was added into the residue, then the mixture was stirred and subjected to liquid separation, the organic phase was dried over anhydrous sodium sulfate and filtered, the organic phase was concentrated to dryness by rotary evaporation to obtain intermediate 1-G, which is yellow oily liquid. LCMS (ESI) m/z: 215 (M+1); $^1$H NMR (400 MHz, CDCl$_3$): δ ppm 1.38 (t, J=7.15 Hz, 3H), 1.90-2.06 (m, 2H), 2.97 (t, J=7.59 Hz, 2H), 3.73 (s, 2H), 4.34 (d, J=7.03 Hz, 2H), 6.81-6.89 (m, 1H), 7.61-7.70 (m, 1H).

Step 6: Synthesis of Intermediate 1-H

Under 20 to 25° C., dichloromethane (19.6 L), 1-G (3916.73 g, 18.3 mol) and ferric chloride (296.83 g, 1.83 mol) were added sequentially into a 50 L reaction kettle, then liquid bromine (1415 mL, 27.5 mol) was added dropwise into the reaction kettle below 10° C., then the reaction was carried out overnight at 15 to 25° C., and the completion of the reaction was monitored by HPLC. Water (20 L) was added into the mixture, then the mixture was stirred and subjected to liquid separation, a saturated sodium thiosulfate solution (20 L) was added into the organic phase and the mixture was stirred and subjected to liquid separation, then water (20 L) was added into the organic phase and the mixture was stirred and subjected to liquid separation, water (20 L) was added into the organic phase again and the mixture was stirred and subjected to liquid separation, the organic phase was concentrated to dryness by rotary evaporation, then the residue was eluted by silica gel column (petroleum ether to petroleum ether/ethyl acetate=3/1), the eluent was concentrated to dryness by rotary evaporation to obtain intermediate 1-H, which is yellow oily liquid. LCMS (ESI) m/z: 295 (M+1); $^1$H NMR (400 MHz, CDCl$_3$): δ ppm 1.36 (t, J=7.15 Hz, 3H), 1.88-2.00 (m, 2H), 2.93 (t, J=7.59 Hz, 2H), 3.66-3.79 (m, 2H), 4.33 (d, J=7.03 Hz, 2H), 7.57-7.66 (s, 1H).

Step 7: Synthesis of Intermediate 1-I

Under 20 to 25° C., 1,4-dioxane (26 L), water (5.2 L), 1-H (3277.79 g, 11.18 mol), 1-D (3300.00 g, 13.50 mol) and anhydrous sodium bicarbonate (2751.12 g, 32.75 mol) were added sequentially into a 50 L reaction kettle, then nitrogen gas was bubbled into the reaction mixture for 15 minutes, then x-PHOS (1044.07 g, 2.19 mol) and Pd$_2$(dba)$_3$ (1000.00 g, 1.09 mol) were added thereto, and the bubbling was continued for about 20 minutes, the reaction was carried out overnight at 110° C. under the protection of nitrogen, and the completion of the reaction was monitored by HPLC. The reaction mixture was cooled to room temperature and filtered, ethyl acetate (22 L) and water (22 L) were added into the filtrate, then the mixture was stirred and subjected to liquid separation, the aqueous phase was extracted once with ethyl acetate (20 L), the combined organic phases were concentrated to dryness by rotary evaporation, methyl tert-butyl ether (20 L) and 2N hydrochloric acid (20 L) were added into the residue, the mixture was stirred and subjected to liquid separation. 2N hydrochloric acid (20 L) was added into the organic phase, then the mixture was stirred and subjected to liquid separation, the aqueous phases were combined and washed with a mixed solution of methyl tert-butyl ether (5 L) and petroleum ether (2.5 L), the pH value of the aqueous phase was adjusted with saturated sodium carbonate at 10 to 20° C. to 7-8, a large amount of solid was precipitated, the mixture was filtered, the solid was collected and dissolved in ethanol (5 L), and activated carbon (300 g) was added thereto, followed by heating and refluxing for half an hour. The mixture was filtered while it was still hot, the filtrate was concentrated to dryness, isopropyl acetate (2 L) was added into the residue and heated to 60° C., the mixture was then slurried and cooled to room temperature and filtered, the solid was collected and dried under pressure to obtain intermediate 1-I, which is pale yellow solid. LCMS (ESI) m/z: 295 (M+1); $^1$H NMR (CDCl$_3$): δ ppm 1.39-1.42 (m, 3H), 1.98-2.04 (m, 2H), 2.17 (s, 2H), 3.16-3.20 (m, 2H), 3.64-3.67 (m, 2H), 4.35-4.41 (m, 2H), 7.43 (s, 1H), 7.79 (s, 1H).

Step 8: Synthesis of Intermediate 1-J

Under 20 to 25° C., dichloromethane (18 L), 1-I (1890.24 g, 6.42 mol), triethylamine (2700 mL, 19.26 mol) and methanesulfonyl chloride (1238 mL, 16.05 mol) were added sequentially into a 50 L reaction kettle, the reaction was carried out while stirring for about 0.5 hour, and the completion of the reaction was monitored by HPLC. 4.5 L of saturated ammonium chloride solution was added into the mixture, then the mixture was stirred and subjected to liquid separation, the aqueous phase was extracted with 4.5 L dichloromethane, the organic phases were combined, dried over anhydrous sodium sulfate and filtered, then the organic phase was concentrated to dryness by rotary evaporation, the residue was transferred to a 50 L reaction kettle, then anhydrous ethanol (18 L), potassium iodide (213.34 g, 1.28 mol) and sodium methoxide (1041.01 g, 19.28 mol) were added thereto, the temperature was raised to 90° C. and the reaction was carried out overnight, and the completion of the reaction was monitored by HPLC. The mixture was cooled to 50 to 60° C., water (18 L) and solid sodium hydroxide (771.12 g, 19.28 mol) were added to the mixture, the reaction was carried out for half an hour under stirring, and the completion of the reaction was monitored by HPLC. The mixture was concentrated under reduced pressure to about 20 L, methyl tert-butyl ether (9 L) were added thereto, then the mixture was stirred and subjected to liquid separation, methyl tert-butyl ether (9 L) was added to the aqueous phase and the mixture was stirred and the liquid was separated, concentrated hydrochloric acid was added to the aqueous phase to adjust the pH value to 3-4, a large amount of solid was precipitated and filtered, the solid was collected and the filter cake was washed with water (1 L×2) and acetone (2.25 L×2) in sequence and filtered, then dried under reduced pressure to obtain intermediate 1-J, which is pale yellow solid. LCMS (ESI) m/z: 249 (M+1); $^1$H NMR (400 MHz, DMSO-d$_6$): δ ppm 2.14 (s, 3H), 2.17-2.21 (m, 2H), 3.07-3.11 (m, 2H), 4.23-4.25 (m, 2H), 7.28 (s, 1H) 7.80 (s, 1H).

Step 9: Synthesis of Intermediate 1-L

Under 20 to 25° C., N,N-dimethylformamide (11.3 L), 1-J (1417.92 g, 5.69 mol), 1-K (2007.29 g, 5.92 mol), and N,N-diisopropylethylamine (2.487 L, 14.24 mol) were added sequentially into a 50 L high and low temperature reaction kettle, the mixture was stirred until complete dissolution of the solid. The mixture was cooled to 0 to 5° C., TBTU (2200.23 g, 6.85 mol) was added in batches, the temperature while adding was controlled below 20° C. After the completion of the addition, the temperature was raise to 20 to 25° C., and temperature was kept and the mixture was stirred 2 hour. The reaction was monitored by HPLC, when the content of 1–J≤0.5%, the reaction was terminated. Ethyl acetate (3 L) and dilute HCl (0.25 N, 34 L) were added sequentially into the mixture under 20 to 25° C., a large amount of solid was precipitated, then the temperature was kept and the mixture was stirred for 10 min. The mixture obtained was filtered and the filter cake was washed with water (7 L×2), the filter cake was added into a 50 L reaction kettle and slurried with methanol (14 L), the mixture was then filtered by a centrifuge, the filter cake was dried naturally for 3 days. The filter cake was detected by HPLC, when the purity ≤98.0% the slurring procedure was repeated, the filter cake was added into a 50 L reaction kettle and slurried with methanol (30 L), then filtered by a centrifuge, the filter cake was dried in vacuum to obtain intermediate 1-L, which is white solid. LCMS (ESI) m/z: 529 (M+1); $^1$H NMR (CDCl$_3$): δ ppm 2.21 (s, 3H), 2.24-2.28 (m, 2H), 2.91-2.93 (m, 1H), 2.98-3.02 (m, 2H), 3.06-3.07 (m, 1H), 3.76-3.78 (m, 1H), 3.83-3.84 (m, 1H), 4.21-4.24 (m, 2H), 4.51-4.52 (m, 1H), 6.82-6.93 (m, 2H), 6.97-7.01 (m, 1H), 7.04-7.08 (m, 1H), 7.21-7.25 (m, 1H), 7.48 (s, 1H), 7.67-7.68 (m, 2H), 7.76-7.78 (dd, J=5.2, 3.0 Hz, 2H).

Step 10: Synthesis of Intermediate 1-M

Under 20 to 25° C., methanol (20 L) and 1-L (2233.25 g, 4.19 mol) were added sequentially into a 50 L high and low temperature reaction kettle, the mixture was then stirred and 98% hydrazine hydrate (1050 mL, 98%, 24.54 mol) was added thereto, the temperature was raised to 80 to 90° C., the reaction was carried out while refluxing for 1.7 hours, a large amount of solid was precipitated. The reaction was detected by HPLC, when the content of 1-L is no more than 0.5%, the reaction was terminated. The mixture was filtered while it was still hot, the filtrate was cooled to 20 to 25° C., a large amount of solid was precipitated and filtered, and the filter cake was washed with methanol (5 L). The filtrate was concentrated to about 1/5 of the original volume (about 5 L), then 20 L of water was slowly poured into the concentrate while stirring, a large amount of solid was precipitated and filtered, the filter cake was washed with water (5 L). Under 20 to 25° C., dilute hydrochloric acid (1 N, 20 L) was added into the filter cake, the mixture was stirred and filtered, the filter cake was washed with water (5 L). The filtrate was transferred into a 50 L dispenser, the mixture was then reverse extracted with the mixed solvent of ethyl acetate and methanol (10/1 (v/v), 11 L×2). The temperature of the aqueous phase was lowered to 0 to 5° C. and the pH value was adjusted with sodium carbonate solid to 8 to 9 while stirring, a large amount of solid was precipitated and filtered, the filter cake was washed with water (2 L) and dried in vacuum to obtain intermediate 1-M, which is white solid. LCMS (ESI) m/z:
399 (M+1); $^1$H NMR (CD$_3$OD): δ ppm 2.23 (s, 3H), 2.24-2.34 (m, 2H), 2.89-2.98 (m, 4H), 3.06-3.09 (m, 2H), 4.23-4.25 (m, 2H), 4.25-4.35 (m, 1H), 6.93-7.02 (m, 1H), 7.04-7.11 (m, 2H), 7.27-7.29 (m, 1H), 7.33 (s, 1H), 7.83 (s, 1H).

Step 11: Synthesis of the Crystal Form of the Compound of Formula (I)

Under 20 to 25° C., methanol (13.2 L) and 1-M (1654.31 g, 3.93 mol) were added sequentially into a 50 L high and low temperature reaction kettle, the temperature was raised to 80 to 90° C., and the mixture was stirred while the temperature was kept for 0.5 hour. The mixture was then filtered while it was still hot, the filtrate was transferred into a 50 L high and low temperature reaction kettle again, the temperature was raised to 80 to 90° C., then a methanol solution of maleic acid (maleic acid 505.94 g dissolved in 1 L methanol, 4.36 mol) was added thereto, and the mixture was stirred while the temperature was kept for 1 hour. The mixture was cooled down gradually, and was stirred for 2 hours while the external temperature was kept at 60 to 70° C., then solid was precipitated. The mixture was then kept at 40 to 50° C. and stirred for 1 hour, then stirred at 20 to 25° C. for 13.5 hours. The mixture was filtered, the filter cake was washed with methanol (500 mL) and dried in vacuum to obtain the crude product of the compound of formula (I). Under 20 to 25° C., methanol (13 L) and the compound of formula (I) (1680 g) were added into a 50 L high and low temperature reaction kettle, the temperature was kept and the mixture was stirred for 3 hours and then filtered, the filter cake was washed with methanol (2 L) and dried in vacuum to obtain the crystal form of the compound of formula (I), which is white powder. LCMS (ESI) m/z: 399 (M+1); $^1$H NMR (CD$_3$OD): δ ppm 2.23 (s, 3H), 2.28-2.39 (m, 2H), 2.97-3.13 (m, 4H), 3.13-3.29 (m, 2H), 4.25 (br d, J=6.0 Hz, 2H), 4.47-4.59 (m, 1H), 6.25 (s, 2H), 6.92-7.02 (m, 1H), 7.03-7.18 (m, 2H), 7.33 (s, 2H), 7.80 (s, 1H).

Characterization Embodiment

Embodiment 1: Stability Test of the Crystal Form of the Compound of Formula (I)

1.1 Experimental Steps:

About 10 mg of the crystal form of the compound of formula (I) was weighed accurately in a dry and clean glass bottle and spread into a thin layer as a formal test sample, the sample was placed under accelerated test conditions (40° C./75% RH and 60° C./75% RH), the sample was completely exposed, covered with aluminum foil paper pierced with small holes. The sample was analyzed after 10 days, 1 month and 2 months. The results are shown in Table 4.

1.2 Preparation of Diluent and Mobile Phase

Diluent: acetonitrile:water (1:1) was used as diluent

For example: 100 mL of pure water and 100 mL of pure acetonitrile were mixed in a glass bottle, followed by degassing with ultrasound for 10 minutes, then cooled down to room temperature.

Mobile phase A: 0.1% phosphoric acid aqueous solution

For example: 2.0 mL phosphoric acid was added into 2000 mL water, followed by ultrasound treatment for 10 minutes, the solution was mixed well and cooled down to room temperature as mobile phase A.

Mobile phase B: acetonitrile

Acetonitrile was used as mobile phase B.

1.3 Preparation of the Reference Solution (0.25 mg/mL Calculated by the Free Base)

The sample of the $0^{th}$ day was used as reference sample, 16 mL of diluent was added thereto, followed by ultrasound treatment for 5 minutes, and the solution was mixed well. Then the solution was further subjected to 1-fold dilution and marked as STD-1 and STD-2, respectively.

1.4 Preparation of Sample Solution for Testing Sensitivity

Reference solution STD-1 (the sample of the $0^{th}$ day) was subjected to 2000-fold dilution, noted as LOQ.

1.5 Preparation of the Sample Solution (0.25 mg/mL Calculated by the Freebase)

The sample was taken out and restored to room temperature and 16 mL diluent was added for dissolution. The solution was further subjected to 1-fold dilution to be used as sample solution to detect the content of related substances.

TABLE 4

Stability test of the crystal form of the compound of formula (I)

| | Impurity content (%) | | | | | | | | |
|---|---|---|---|---|---|---|---|---|---|
| | −20° C. | | | 40° C./75%RH | | | 60° C./75%RH | | |
| RRT | 10D | 1M | 2M | 10D | 1M | 2M | 10D | 1M | 2M |
| 0.95 | 0.04 | 0.04 | 0.04 | | 0.05 | 0.04 | | 0.05 | 0.04 |
| 0.98 | 0.10 | 0.11 | 0.10 | 0.10 | 0.10 | 0.10 | 0.10 | 0.10 | 0.10 |
| 0.99 | 1.37 | 1.38 | 1.35 | 1.40 | 1.36 | 1.31 | 1.36 | 1.27 | 1.22 |
| 1.02 | 0.29 | 0.22 | 0.19 | 0.24 | 0.22 | 0.20 | 0.24 | 0.19 | 0.24 |
| 1.04 | 0.07 | 0.05 | 0.04 | 0.04 | 0.05 | 0.04 | 0.07 | 0.08 | 0.08 |
| 1.06 | | | | 0.05 | 0.09 | 0.15 | 0.34 | 0.45 | |
| 1.21 | 1.47 | 1.52 | 1.51 | 1.50 | 1.50 | 1.44 | 1.46 | 1.44 | 1.43 |
| 1.26 | 0.05 | 0.07 | 0.10 | 0.06 | 0.07 | 0.06 | 0.09 | 0.10 | 0.10 |
| 1.33 | | | | | | | | | 0.06 |
| 1.36 | | | | | | | | | 0.08 |
| 1.43 | | 0.05 | | | 0.09 | | | | 0.05 |
| TRS (%) | 3.39 | 3.38 | 3.38 | 3.35 | 3.38 | 3.37 | 3.47 | 3.57 | 3.85 |

RRT: retention time relative to main peak; TRS: total impurity content; RH: relative humidity.

According to the experimental results, the crystal form of the compound of formula (I) are stable under the conditions of high temperature and high humidity, the impurity content is basically unchanged.

Embodiment 2: Solubility Test of the Crystal Form of the Compound of Formula (I)

2.1 Experimental Steps:

10 mg of the crystal form of the compound of formula (I) was weighed accurately and placed in a glass bottle, 1 mL solvent was added thereto, the solution was shaken vigorously for 30 seconds every 5 minutes under 25±2° C., the dissolution phenomenon within 30 minutes was observed. The corresponding data was recorded.

1 mg of the insoluble sample in step 2.1 was weighed accurately and placed in a glass bottle, a suitable solvent was added thereto, the solution was shaken vigorously for 30 seconds every 5 minutes under 25±2° C., the dissolution phenomenon within 30 minutes was observed. The corresponding data was recorded.

TABLE 5

Scales used for the solubility evaluation

| Compound added (mg) | Total amount of the solvent added (mL) | Solubility classification |
|---|---|---|
| 100 | 0.1 | Extremely soluble |
| 10 | 0.1 | Quite soluble |
| | 0.3 | Soluble |
| | 1 | Relatively soluble |
| 1 | 1 | Slightly soluble |
| | 10 | Minimally soluble |
| 1 | >10 | Barely soluble or insoluble |

TABLE 6

Approximate solubility of the crystal form of the compound of formula (I) in different solvent

| Solvent | Solubility classification | Solvent | Solubility classification |
|---|---|---|---|
| Dimethyl sulfoxide | Quite soluble | Water | Barely soluble or insoluble |
| Methanol | Slightly soluble | 0.1N HCl | Minimally soluble |
| N-Methylpyrrolidone | Quite soluble | 0.1N NaOH | Barely soluble or insoluble |
| Acetonitrile | Barely soluble or insoluble | | |

It can be seen from the experimental results that the crystal form of the compound of formula (I) is quite soluble in dimethyl sulfoxide or N-methylpyrrolidone, slightly soluble in methanol, and barely soluble or insoluble in acetonitrile or water; it is barely soluble or insoluble in 0.1 N hydrochloric acid or 0.1 N sodium hydroxide solution.

Embodiment 3: Hygroscopicity Test of the Crystal Form of the Compound of Formula (I)

Experimental Procedure:

Three dry glass weighing bottles (with an outer diameter of 50 mm and a height of 30 mm) with a stopper was placed in a desiccator with saturated ammonium chloride solution at the lower part, the glass weighing bottles were left open, the desiccator was covered with lid, and then the desiccator was placed in a 25° C. incubator and left overnight.

The weighing bottle was weighed precisely after placed overnight, the weight was respectively $m_1$ 1, $m_1$ 2, $m_1$ 3

An appropriate amount of the crystal form of the compound of formula (I) was laid flat in the weighing bottles which was already weighed (with the sample thickness of about 1 mm), and was weighed precisely, the weight was respectively $m_2$ 1, $m_2$ 2, $m_2$ 3.

The weighing bottle was left open and was placed together with the stopper in a desiccator with saturated ammonium chloride solution at the lower part, the weighing bottle was left open, the desiccator was covered with lid, and then the desiccator was placed in a 25° C. incubator for 24 hours.

The weighing bottle was covered with its stopper after placed for 24 hours, and then it was weighed precisely, the weight was respectively $m_3$ 1, $m_3$ 2, $m_3$ 3.

The hygroscopic weight gain was calculated, the calculation formula is as follows:

$$\text{Weight gain percentage} = 100\% \times (m_3 - m_2)/(m_2 - m_1)$$

TABLE 7

Hygrosopicity situation table of the crystal form of the compound of formula (I)

| Sample | $m_1$ (mg) | $m_2$ (mg) | $m_3$ (mg) | Weight gain percentage (%) | Average (%) |
|---|---|---|---|---|---|
| 1 | 34624.75 | 35628.44 | 35629.67 | 0.12 | 0.07 |
| 2 | 36260.98 | 37262.55 | 37263.00 | 0.04 | |
| 3 | 34955.71 | 35957.15 | 35957.67 | 0.05 | |

According to the result of the hygrosopicity test, the average hygrosopicity of the crystal form of the compound of formula (I) is 0.07%<0.2%, therefore, the crystal form of the compound of formula (I) almost has no or almost no hygroscopicity.

Embodiment 4: Infrared Absorption Test of the Crystal Form of the Compound of Formula (I)

Instrument: Nicolet 6700 FT-IR type infrared spectrometer

Method: ART attenuation total reflection method

The infrared absorption spectrum of the crystal form of the compound of formula (I) is as shown in FIG. 4.

TABLE 8

Infrared absorption test result of the crystal form of the compound of formula (I)

| Absorption peak wave number ($cm^{-1}$) | Type of vibration | Group | Absorption peak intensity |
|---|---|---|---|
| 3316 | stretching vibration of N—H | amido | m |
| 3079, 3058, 3016 | stretching vibration of =C—H | benzene ring, aromatic heterocycle, alkenyl | w, w, w |
| 2954-2864 | symmetric or asymmetric stretching vibration of C—H | —CH—, —CH$_2$—, —CH$_3$ | w, w, w, w, w |
| 3316-2864 | stretching vibration of NH$_3^+$ | amine salt | m, w, w, w, w, w, w, w, w |
| 1704-1445 | stretching vibration of C=O, stretching vibration of C=C and C=N, anti symmetric stretching vibration of carboxylate | carboxyl, amido, benzene ring, aromatic heterocycle, alkenyl | m, s, s, w, m, s, s, s |
| 1486-1373 | deformation vibration of C—H, symmetric stretching carboxyl vibration of carboxylate | —CH—, —CH$_2$—, —CH$_3$, | s, s, m, w, m, m |
| 1359-1000 | stretching vibration of C—F and C—N, in plane bending vibration of C—H | amino, C—F bond, benzene ring, aromatic heterocycle, alkenyl | s, m, m, m, m, s, m, m, w, m, m, m |
| 952-704 | out-of-plane bending vibration of =C—H, N—H stretching vibration | carboxyl, amido, amine salt, benzene ring, aromatic heterocycle, alkenyl | m, m, w, m, s, m, w, m, s, m, w, m | s: represents for a strong peak;
m: represents for a medium intensity peak;
w: represents for a weak peak.

Infrared Spectrum Analysis:

1) 3316 $cm^{-1}$: stretching vibration of N—H; 1704-1623 $cm^{-1}$: stretching vibration of C=O; 1359-1000 $cm^{-1}$: stretching vibration of C—N; 952-704 $cm^{-1}$: out-of-plane bending vibration of =C—H; proving that the structure of the sample contains amide;

2) 3079, 3058, 3016 $cm^{-1}$: stretching vibration of =C—H; 1704-1445 $cm^{-1}$; stretching vibration of C=C and C=N; 1359-1000 $cm^{-1}$: in plane bending vibration of C—H; 952-704 $cm^{-1}$: out-of-plane bending vibration of =C—H; proving that the structure of the sample contains benzene ring, aromatic heterocycle and akenyl;

3) 2954-2864 $cm^{-1}$: symmetric or asymmetric stretching vibration of C—H; 1486-1373 $cm^{-1}$: deformation vibration of C—H; proving that the structure of the sample contains the structure of —CH—, —CH$_2$— and —CH$_3$;

4) 3316-2864 $cm^{-1}$: stretching vibration of NH$_3^+$; 1359-1000 $cm^{-1}$: stretching vibration of C—N; 952-704 $cm^{-1}$: stretching vibration of N—H; proving that the structure of the sample contains amine salt; 1633-1530 $cm^{-1}$: antisymmetric stretching vibration of carboxylate; 1445-1395 $cm^{-1}$: symmetric stretching vibration of carboxylate; proving that the structure of the sample contains carboxylate;

5) 1359-1000 $cm^{-1}$: stretching vibration of C—F; proving that the structure of the sample contains C—F bond;

The error range complies with the requirements of the "Chinese Pharmacopoeia", i.e. an error tolerance of ±5 $cm^{-1}$ can exist near 3000 $cm^{-1}$, and an error tolerance of ±2 $cm^{-1}$ can exist near 1000 $cm^{-1}$.

According to the infrared spectrum, the structure of the sample contains amide, benzene ring, aromatic heterocycle, alkenyl, —CH—, —CH$_2$—, —CH$_3$, amine salt, carboxylate and C—F bond structure. The above IR spectrum results are consistent with the structure of the crystal form of the compound of formula (I).

Embodiment 5: Ultraviolet Absorption Test of the Crystal Form of the Compound of Formula (I)

Instrument: Agilent 8453 ultraviolet-visible spectrophotometer

Solvent: methanol/pure water=1/1 (v/v)

Mother liquor: 10.198 mg of a sample of the crystal form of the compound of formula (I) was weighed and placed in a 100 mL volumetric flask, then the sample was fully dissolved and diluted to the scale by adding the diluent (methanol/pure water=1/1 (v/v)), then the solution was mixed well.

Test solution: 2.2 mL of mother liquor was pipetted into a 10 mL volumetric flask, the solution was diluted to the scale by adding the diluent (methanol/pure water=1/1 (v/v)), and the solution was mixed well to obtain a sample solution with a concentration of 4.3601×10−5 mol/L.

Wavelength measured: 200-700 nm

Figure 5:
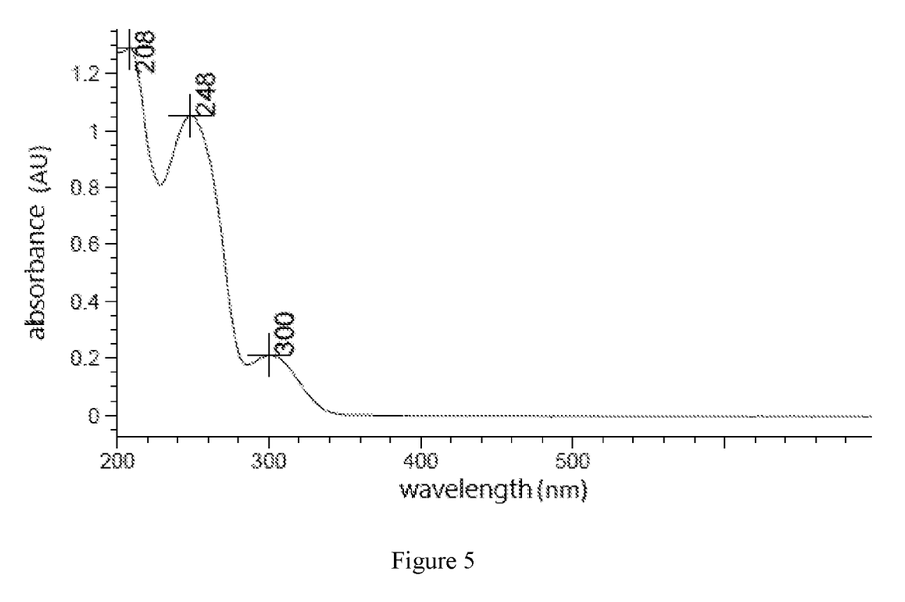
FIG. 5 is the ultraviolet absorption spectrogram of the crystal form of the compound of formula (I).

The ultraviolet spectrum of the sample in methanol is as shown in FIG. 5.

TABLE 9

Ultraviolet absorption test result of the crystal form of the compound of formula (I)

| solvent | $\lambda_{max}$ (nm) | $\varepsilon$ (M$^{-1}$cm$^{-1}$) |
|---|---|---|
| methanol/pure water = 1/1 (v/v) | 208 | 29662 |
|  | 248 | 24137 |
|  | 300 | 4804 |

In methanol, $\lambda_{max}$=208 nm is the E band characteristic absorption of aromatic heterocycle, $\lambda_{max}$=248 nm is the B band characteristic absorption of aromatic ring, $\lambda_{max}$=300 nm is the K band characteristic absorption of aromatic ring.

Activity Test

Embodiment 1: AKT Enzyme Activity Test of the Crystal Form of the Compound of Formula (I)

AKT, also known as protein kinase B (PKB), is a serine/threonine specific protein kinase, mainly including AKT1, AKT2 and AKT3. The AKT signaling pathway plays an important role in various cellular processes such as glucose metabolism, apoptosis, cell proliferation transcription and cell migration. This study intends to analyze the inhibitory effect of the crystal form of the compound of formula (I) on the kinase activity of AKT family members.

Reagents and Consumables:

ULight-CREBtide (PerkinElmer TRF0107-M, batch 2035700)

Europium-Anti-P-CREB (Ser-133) (PerkinElmer TRF0200-M, batch 2002391)

LANCE Detection Buffer, 10* (PerkinElmer CR97-100)

ATP (Invitrogen PV3227)

Akt1 protein (life technology batch 11629928C)

Akt2 protein (life technology batch 28870GG)

Akt3 protein (life technology batch 1715050B)

384 wells plate_detection plate (PerkinElmer 6007299)

Experimental Principle:

In this experiment, the homogeneous time-resolved fluorescence conjugated energy transfer (LANCE TR-FRET®) method was used. The enzymes, biotinylated polypeptide substrates and the compound to be tested were mixed in the detection plate, and ATP was added to initiate the reaction and the mixture was incubated. After the reaction, EDTA was added to terminate the reaction, and Eu-labeled antibody was added at the same time to carry out the reaction and the reaction was detected. The detection plate was analyzed using Envision from PE Company, and the analysis mode was TR-FRET, the data were expressed by fluorescence signals at 665 nm and 615 nm, respectively. Wherein, a high ratio of 665 nm/615 nm indicates high activity, while a low ratio of 665 nm/615 nm indicates that the activity is inhibited.

Experimental Method:

Compound preparation: the test compound and the reference compound were diluted with 100% DMSO, the initial concentrations of the compounds were 10 µM, and the compounds were 3-fold gradient diluted into 10 concentrations. The compound was then transferred into the cell plate and double duplicate well experiment was set up.

Kinase detection: the enzyme and the substrate were mixed with different concentrations of pre-diluted compounds, and the final concentrations of Akt1, Akt2, and Akt3 kinase were 1.25 nM, 2 nM, and 2 nM, respectively. The solutions were left at room temperature for 15 minutes, double duplicate wells were prepared for each concentration. ATP was added with final concentrations of 36 µM, 360 µM, and 160 µM in the Akt1, Akt2, and Akt3 kinase reactions, respectively, and the reaction was carried out at room temperature for 90 minutes (in which positive and negative controls were set). After completion of the reaction, the antibody was added for detection, the samples were incubated at room temperature for 60 minutes, detection was performed by Evnvision and data was collected. Data analysis and fitting was performed according to *Lfit5 software.

Experimental Results: see Table 10.

TABLE 10

IC$_{50}$ value of the inhibition of the crystal form of the compound of formula (I) on kinase activity

| Compound | IC$_{50}$ (nM) | | |
|---|---|---|---|
|  | AKT1 | AKT2 | AKT3 |
| Crystal form of the compound of formula (I) | 1.30 | 50.3 | 90.4 |

The result of this experiment shows: the crystal form of the compound of formula (I) have strong inhibition effect against the activity of AKT1, AKT2 and AKT3 kinase, wherein the inhibitory effect against the activity of AKT1 kinase is the most significant.

Embodiment 2: Cytoactive Test of the Compound of Formula (I)

This experiment intends to study the inhibitory effect of the compound of formula (I) on the prostate cancer cell LNCaP overexpressing AKT.

Reagents and Consumables:

1. Cell culture: RPMI-1640 medium, fetal bovine serum, Accutase, DPBS

2. Cell line: LNCaP

3. Detection reagent: live cell detection kit CellTiter-Glo

4. Other main consumables and reagents: compound dilution plate, intermediate plate, detection plate, DMSO Experimental Principle:

The content of ATP directly reflects the number and state of cells, and the number of living cells can be detected by quantitatively measuring ATP. The live cell detection kit contains luciferase and its substrate, with the participation of ATP, luciferase can catalyze the substrate and emit a stable optical signal, the amount of ATP in the cell can be determined by detecting the strength of the signal. Wherein the light signal is proportional to the amount of ATP in the cell, and ATP is positively correlated to the number of living cells, so that the proliferation of the cell can be detected. The detection plate was analyzed by using Envision from PE Company.

Experimental Method:
1. Preparation of Cell Plate
LNCaP cells were seeded in a 384-well plate, each well contained 1000 cells.
The cell plate was placed in a carbon dioxide incubator overnight.
2. Preparation of the Compound
The compound was 3-fold diluted with Bravo into 10 compound concentrations, and a double duplicate well experiment was set up.
3. Treatment of the Cells with the Compound
The compound was transferred to the cell plate at an initial concentration of 10 μM. The cell plate was placed in a carbon dioxide incubator for 3 days.
4. Detection
Promega CellTiter-Glo reagent was added to the cell plate, and incubated at room temperature for 10 minutes to stabilize the luminescence signal, which was read by PerkinElmer Envision multi-label analyzer.
Experimental Results: See Table 11.

TABLE 11

$IC_{50}$ value of the inhibition of the crystal form of the compound of formula (I) on cell proliferation

| Cell line | $IC_{50}$ (nM) crystal form of the compound of formula (I) |
|---|---|
| LNCaP | 67 |

The result of this experiment shows: the crystal form of the compound of formula (I) has a significant inhibitory effect on the growth of AKT-overexpressing cells LNCaP.

What is claimed is:
1. A compound of formula (I),

(I)

2. A crystal form of the compound of formula (I), wherein the X-ray powder diffraction pattern thereof comprises characteristic diffraction peaks at the following angle 2θ: 12.25°±0.2°, 14.46°±0.2° and 21.83°±0.2°, (I)

3. The crystal form of the compound of formula (I) as defined in claim 2, wherein the X-ray powder diffraction pattern thereof comprises characteristic diffraction peaks at the following angle 2θ: 8.50°±0.2°, 10.20°±0.2°, 12.25°±0.2°, 14.46°±0.2°, 15.30°±0.2°, 21.83°±0.2°, 27.31°±0.2° and 31.41°±0.2°.
4. The crystal form of the compound of formula (I) as defined in claim 3, wherein the X-ray powder diffraction pattern thereof is as shown in FIG. 1.
5. The crystal form of the compound of formula (I) as defined in claim 2, wherein the DSC pattern of the crystal form has an endothermic peak with an onset of 195.10° C. ±3° C., and has an exothermic peak with an onset of 209.23° C. ±3° C.
6. The crystal form of the compound of formula (I) as defined in claim 5, wherein the DSC pattern of the crystal form is as shown in FIG. 2.
7. The crystal form of the compound of formula (I) as defined in claim 2, wherein the TGA pattern of the crystal form has a weight loss of 0.295% occurred at 100.00° C. ±3° C.
8. The crystal form of the compound of formula (I) as defined in claim 7, wherein the TGA pattern of the crystal form is as shown in FIG. 3.
9. The crystal form of the compound of formula (I) as defined in claim 2, wherein the infrared spectrum of the crystal form comprises characteristic absorption peaks at 3316 cm$^{-1}$±5 cm$^{-1}$, 3079cm$^{-1}$±5 cm$^{-1}$, 3058 cm$^{-1}$±5 cm$^{-1}$, 3016 cm$^{-1}$±5 cm$^{-1}$, 2954 cm$^{-1}$±5 cm$^{-1}$, 2935 cm$^{-1}$±5 cm$^{-1}$, 2915 cm$^{-1}$±5 cm$^{-1}$, 2902 cm$^{-1}$±5 cm$^{-1}$, 2864 cm$^{-1}$±5 cm$^{-1}$, 1704 cm$^{-1}$ ±2 cm$^{-1}$, 1633 cm$^{-1}$±2 cm$^{-1}$, 1623 cm$^{-1}$±2 cm$^{-1}$, 1589 cm$^{-1}$±2 cm$^{-1}$, 1530 cm$^{-1}$±2 cm$^{-1}$, 1514 cm$^{-1}$±2 cm$^{-1}$, 1486 cm$^{-1}$±2 cm$^{-1}$, 1445 cm$^{-1}$±2 cm$^{-1}$, 1429 cm$^{-1}$±2 cm$^{-1}$, 1408 cm$^{-1}$±2 cm$^{-1}$, 1395 cm$^{-1}$±2 cm$^{-1}$, 1373 cm$^{-1}$±2 cm$^{-1}$, 1359 cm$^{-1}$±2 cm$^{-1}$, 1345 cm$^{-1}$±2 cm$^{-1}$, 1332 cm$^{-1}$±2 cm$^{-1}$, 1282 cm$^{-1}$±2 cm$^{-1}$, 1247 cm$^{-1}$±2 cm$^{-1}$, 1214 cm$^{-1}$±2 cm$^{-1}$, 1173 cm$^{-1}$±2 cm$^{-1}$, 1135 cm$^{-1}$±2 cm$^{-1}$, 1114 cm$^{-1}$±2 cm$^{-1}$, 1054 cm$^{-1}$±2 cm$^{-1}$, 1030 cm$^{-1}$±2 cm$^{-1}$, 1000 cm$^{-1}$±2 cm$^{-1}$, 952 cm$^{-1}$±2 cm$^{-1}$, 914 cm$^{-1}$±2 cm$^{-1}$, 902 cm$^{-1}$±2 cm$^{-1}$, 883 cm$^{-1}$±2 cm$^{-1}$, 861 cm$^{-1}$±2 cm$^{-1}$, 839 cm$^{-1}$±2 cm$^{-1}$, 825 cm$^{-1}$±2 cm$^{-1}$, 789 cm$^{-1}$±2 cm$^{-1}$, 763 cm$^{-1}$±2 cm$^{-1}$, 736 cm$^{-1}$±2 cm$^{-1}$, 720 cm$^{-1}$±2 cm$^{-1}$ and 704 cm$^{-1}$±2 cm$^{-1}$.
10. The crystal form of the compound of formula (I) as defined in claim 9, wherein the infrared spectrum thereof is as shown in FIG. 4.
11. A method for treating prostate cancer, diabetes or rheumatoid arthritis in a subject in need thereof, comprising administering an effect amount of the compound of formula (I) as defined in claim 1 to the subject.
12. A method for treating prostate cancer, diabetes or rheumatoid arthritis in a subject in need thereof, comprising administering an effect amount of the crystal form of the compound of formula (I) as defined in claim 2 to the subject.
13. A method for treating prostate cancer, diabetes or rheumatoid arthritis in a subject in need thereof, comprising administering an effect amount of the crystal form of the compound of formula (I) as defined in claim 3 to the subject.
14. A method for treating prostate cancer, diabetes or rheumatoid arthritis in a subject in need thereof, comprising administering an effect amount of the crystal form of the compound of formula (I) as defined in claim 4 to the subject.
15. The crystal form of the compound of formula (I) as defined in claim 3, wherein the DSC pattern of the crystal form has an endothermic peak with an onset of 195.10° C. ±3° C., and has an exothermic peak with an onset of 209.23° C. ±3° C.

16. The crystal form of the compound of formula (I) as defined in claim 4, wherein the DSC pattern of the crystal form has an endothermic peak with an onset of 195.10° C. ±3° C., and has an exothermic peak with an onset of 209.23° C. ±3° C.

17. The crystal form of the compound of formula (I) as defined in claim 3, wherein the TGA pattern of the crystal form has a weight loss of 0.295% occurred at 100.00° C. ±3° C.

18. The crystal form of the compound of formula (I) as defined in claim 4, wherein the TGA pattern of the crystal form has a weight loss of 0.295% occurred at 100.00° C. ±3° C.

19. The crystal form of the compound of formula (I) as defined in claim 3, wherein the infrared spectrum of the crystal form comprises characteristic absorption peaks at 3316 cm$^{-1}$±5 cm$^{-1}$, 3079 cm$^{-1}$±5 cm$^{-1}$, 3058 cm$^{-1}$±5 cm$^{-1}$, 3016 cm$^{-1}$±5 cm$^{-1}$, 2954 cm$^{-1}$±5 cm$^{-1}$, 2935 cm$^{-1}$±5 cm$^{-1}$, 2915 cm$^{-1}$±5 cm$^{-1}$, 2902 cm$^{-1}$±5 cm$^{-1}$, 2864 cm$^{-1}$±5 cm$^{-1}$, 1704 cm$^{-1}$±2 cm$^{-1}$, 1633 cm$^{-1}$±2 cm$^{-1}$, 1623 cm$^{-1}$±2 cm$^{-1}$, 1589 cm$^{-1}$±2 cm$^{-1}$, 1530 cm$^{-1}$±2 cm$^{-1}$, 1514 cm$^{-1}$±2 cm$^{-1}$, 1486 cm$^{-1}$±2 cm$^{-1}$, 1445 cm$^{-1}$±2 cm$^{-1}$, 1429 cm$^{-1}$±2 cm$^{-1}$, 1408 cm$^{-1}$±2 cm$^{-1}$, 1395 cm$^{-1}$±2 cm$^{-1}$, 1373 cm$^{-1}$±2 cm$^{-1}$, 1359 cm$^{-1}$±2 cm$^{-1}$, 1345 cm$^{-1}$±2 cm$^{-1}$, 1332 cm$^{-1}$±2 cm$^{-1}$, 1282 cm$^{-1}$±2 cm$^{-1}$, 1247 cm$^{-1}$±2 cm$^{-1}$, 1214 cm$^{-1}$±2 cm$^{-1}$, 1173 cm$^{-1}$±2 cm$^{-1}$, 1135 cm$^{-1}$±2 cm$^{-1}$, 1114 cm$^{-1}$±2 cm$^{-1}$, 1054 cm$^{-1}$±2 cm$^{-1}$, 1030 cm$^{-1}$±2 cm$^{-1}$, 1000 cm$^{-1}$±2 cm$^{-1}$, 952 cm$^{-1}$±2 cm$^{-1}$, 914 cm$^{-1}$±2 cm$^{-1}$, 902 cm$^{-1}$±2 cm$^{-1}$, 883 cm$^{-1}$±2 cm$^{-1}$, 861 cm$^{-1}$±2 cm$^{-1}$, 839 cm$^{-1}$±2 cm$^{-1}$, 825 cm$^{-1}$±2 cm$^{-1}$, 789 cm$^{-1}$±2 cm$^{-1}$, 763 cm$^{-1}$±2 cm$^{-1}$, 736 cm$^{-1}$±2 cm$^{-1}$, 720 cm$^{-1}$±2 cm$^{-1}$ and 704 cm$^{-1}$±2 cm$^{-1}$.

20. The crystal form of the compound of formula (I) as defined in claim 2, wherein the analytical data of the X-ray powder diffraction pattern thereof is as shown in the following table.

| No. | 2θ Angle (°) | d-spacing (Å) | Relative intensity (%) |
|---|---|---|---|
| 1 | 4.860 | 18.169 | 1.0 |
| 2 | 5.139 | 17.181 | 2.0 |
| 3 | 5.373 | 16.434 | 0.8 |
| 4 | 7.273 | 12.145 | 4.9 |
| 5 | 8.503 | 10.390 | 39.7 |
| 6 | 10.202 | 8.663 | 37.7 |
| 7 | 12.254 | 7.217 | 53.0 |
| 8 | 13.668 | 6.474 | 12.1 |
| 9 | 13.815 | 6.405 | 14.1 |
| 10 | 14.460 | 6.121 | 100.0 |
| 11 | 15.303 | 5.785 | 69.3 |
| 12 | 15.578 | 5.684 | 6.7 |
| 13 | 17.797 | 4.980 | 0.7 |
| 14 | 18.632 | 4.759 | 7.7 |
| 15 | 19.091 | 4.645 | 1.4 |
| 16 | 19.876 | 4.463 | 6.1 |
| 17 | 20.449 | 4.440 | 2.0 |
| 18 | 21.031 | 4.221 | 3.2 |
| 19 | 21.834 | 4.067 | 42.5 |
| 20 | 22.448 | 3.957 | 14.5 |
| 21 | 22.859 | 3.887 | 28.4 |
| 22 | 23.106 | 3.846 | 5.5 |
| 23 | 24.060 | 3.696 | 14.6 |
| 24 | 24.591 | 3.617 | 2.6 |
| 25 | 25.574 | 3.480 | 3.9 |
| 26 | 25.593 | 3.478 | 3.6 |
| 27 | 26.733 | 3.332 | 22.0 |
| 28 | 27.310 | 3.263 | 24.4 |
| 29 | 27.771 | 3.210 | 10.1 |
| 30 | 28.441 | 3.136 | 4.1 |
| 31 | 28.571 | 3.122 | 4.3 |
| 27 | 29.106 | 3.066 | 2.7 |
| 28 | 29.594 | 3.016 | 2.0 |
| 29 | 30.229 | 2.954 | 1.2 |
| 30 | 30.837 | 2.897 | 21.5 |
| 31 | 31.409 | 2.846 | 27.6 |
| 32 | 32.829 | 2.726 | 2.0 |
| 33 | 32.513 | 2.752 | 1.1 |
| 34 | 32.832 | 2.726 | 1.8 |
| 35 | 33.201 | 2.696 | 3.1 |
| 36 | 33.800 | 2.650 | 4.2 |
| 37 | 34.771 | 2.578 | 0.7 |
| 38 | 35.149 | 2.551 | 0.9 |
| 39 | 35.402 | 2.533 | 1.6 |
| 40 | 36.021 | 2.491 | 2.0 |
| 41 | 36.764 | 2.443 | 7.0 |
| 42 | 37.624 | 2.389 | 2.4 |
| 43 | 37.724 | 2.383 | 3.0 |
| 44 | 38.410 | 2.342 | 2.5 |
| 45 | 39.218 | 2.295 | 1.0 |
| 46 | 39.516 | 2.279 | 1.2. |

* * * * *